US006881425B2

(12) United States Patent
Pushpangadan et al.

(10) Patent No.: US 6,881,425 B2
(45) Date of Patent: Apr. 19, 2005

(54) CUSTOM MADE HERBAL HEALTH PROMOTIVE FORMULATION FOR FEMALES/EXPECTANT MOTHERS

(75) Inventors: Palpu Pushpangadan, Lucknow (IN); Dhan Prakash, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 155 days.

(21) Appl. No.: 09/944,261

(22) Filed: Aug. 31, 2001

(65) Prior Publication Data

US 2003/0129258 A1 Jul. 10, 2003

(51) Int. Cl.$^7$ .............................................. A61K 35/78

(52) U.S. Cl. ....................... 424/725; 424/750; 424/757; 424/776

(58) Field of Search ................................ 424/725, 750, 424/757, 776

(56) References Cited

PUBLICATIONS

V. mungo (Linn.), *The Wealth of India: A Dictionary of Indian Raw Materials & Industrial Products*, National Institute of Science Communication; Counsel of Scientific & Industrial Research, Pusa, New Delhi, India 110–102; vol. 10, 1982, p., 476, 481–484; 490–492; 494–495.

Amaranthus Linn., *The Wealth of India: A Dictionary of Indian Raw Materials & Industrial Products*, National Institute of Science Communication; Counsel of Scientific & Industrial Research, Pusa, New Delhi, India 110–102; vol. 1, 1985, p., 213–214, 216–217.

Prakash et al.; "Seed Protein, Fat and Fatty Acid Profile of Amaranthus Species", *J Sci Food Agric*, 1992, vol. 58, pp. 145 Abstract.

Prakash et al., "Nutritional and Antinutritional Composition of Vegetable and Grain Amaranth Leaves", *J Sci Food Agric*, 1991, vol. 57, p. 573 Abstract.

Chenopodium Linn, *The Wealth of India: A Dictionary of Indian Raw Materials & Industrial Products*, National Institute of Science Communication; Counsel of Scientific & Industrial Research, Pusa, New Delhi, India 110–102; vol. III, 1992, pp. 464; 472.

Chenopodium album L., *A Lexicon of Medicinal Plants in India,*, 1999, vol.. 1, pp 424–425.

Prakash et al., "Composition, Variation of Nutritional Contents in Leaves, Seed Protein, Fat and Fatty Acid Profile of Chenopodium Species", *J Sci Food Agric*, 1993, vol. 62, pp. 203 Abstract.

Prakash et al., "*Chenopodium quinoa*: changes in amino acid composition in seed during maturity", International Journal of Food Sciences and Nutrition, 1998, vol. 49, p. 285 Abstract.

C. arietinum Linn, *The Wealth of India: A Dictionary of Indian Raw Materials & Industrial Products*, National Institute of Science Communication; Counsel of Scientific & Industrial Research, Pusa, New Delhi, India 110–102; vol. 10, 1982, pp. 526–527; 550–554.

Fagopyrum Moench, *The Wealth of India: A Dictionary of Indian Raw Materials & Industrial Products*, National Institute of Science Communication; Counsel of Scientific & Industrial Research, Pusa, New Delhi, India 110–102, vol. 4, 1956, pp. 1–4.

Prakash et al., "Protein and amino acid composition of Fagoypyrum (buckwheat)" *Plant Foods for Human Nutrition*, 1987, vol. 36, p. 341 Abstract.

Quettier–Deleu et al., "Phenolic compounds and antioxidant activities of buckwheat (*Fagopyrum esculentum* Moench) hulls and flour", J of Ethnopharmacology, 2000, vol. 72, pp 35–36; 40–42.

Elettaria, *The Wealth of India: A Dictionary of Indian Raw Materials & Industrial Products*, National Institute of Science Communication; Counsel of Scientific & Industrial Research, Pusa, New Delhi, India 110–102, vol. 3, 2000, pp. 149–150; 156–157.

Glycine Linn, *The Wealth of India: A Dictionary of Indian Raw Materials & Industrial Products*, National Institute of Science Communication; Counsel of Scientific & Industrial Research, Pusa, New Delhi, India 110–102; vol. 4, 2000, pp. 142, 146–148.

(Continued)

*Primary Examiner*—Brenda Brumback
*Assistant Examiner*—Randall Winston
(74) *Attorney, Agent, or Firm*—RatnerPrestia

(57) ABSTRACT

The present invention relates to a herbal health protective, promotive neutraceutical formulation for women, human expectant mothers and lactating mothers, and also relates to a process for the preparation of custom made herbal health protective, promotive nutraceutical formulations as food supplements to ameliorate the general health of females with optimum nutrients, said process comprises the base product of microwave oven roasted seed powders mixture from selected genera of Glycine, Phaseolus, Cicer, Psophocarpus, Mucuna, Triticum, Hordeum, Amaranthus, Chenopodium and Fagopyrum, fortified with the natural herbs/medicinal plants extract from the genera Centella, Withania, Pueraria, Asparagus, Chlorophytum, Boerhaavia, Sida, Saraca and also some other ingredients like pale sugar powder, jaggary, milk powder, coca powder, *Elettaria cardamomum* (Elaichi) powder, *Piper longum* (Pippali) fruit powder, *Myristica fragrans* (Jaiphal) fruit powder were also added to get the final nutraceuticals; the nutraceuticals are with optimum natural nutrients, non toxic, natural herbal plant products, easy to digest, have protective, preventive and health promotive properties for the good health and vigour of the females, pregnant and lactating mothers so as to ensure the optimal growth and development of the child both at prenatal and post natal stages.

10 Claims, No Drawings

OTHER PUBLICATIONS

Hordeum Linn, *The Wealth of India: A Dictionary of Indian Raw Materials & Industrial Products*, National Institute of Science Communication; Counsel of Scientific & Industrial Research, Pusa, New Delhi, India 110–102; vol. 5, 2000, pp. 117–119.

P. *vulgaris* Linn, *The Wealth of India: A Dictionary of Indian Raw Materials & Industrial Products*, National Institute of Science Communication; Counsel of Scientific & Industrial Research, Pusa, New Delhi, India 110–102; CSIR, 2000, pp. 8; 11–12.

P. *tuberosa* DC, *The Wealth of India: A Dictionary of Indian Raw Materials & Industrial Products*, National Institute of Science Communication; Counsel of Scientific & Industrial Research, Pusa, New Delhi, India 110–102; CSIR, 2000, pp. 316–317.

Jani et al., "*Pueraria tuberosa*: An Overview", *Indian Drugs*, Dec. 1981 p 93 Abstract.

Ali et al., "Studies on the Peptide and Amino Acids of *Pueraria tuberosa*", *J Indian Chem. Soc.*, vol. LXIII, Oct. 1986, p. 918 Abstract.

T. *aestivum* Linn, *The Wealth of India: A Dictionary of Indian Raw Materials & Industrial Products*, National Institute of Science Communication; Counsel of Scientific & Industrial Research, Pusa, New Delhi, India 110–102; vol. 10, 1982, p 315, 360–362; 367–368.

Psophocardus DC, *The Wealth of India: A Dictionary of Indian Raw Materials & Industrial Products*, National Institute of Science Communication; Counsel of Scientific & Industrial Research, Pusa, New Delhi, India 110–102; CSIR, 2000, pp. 294–295.

Misra et al., "Assay of some nutritional and antinutritional factors in different cultivars of winged bean (*Psophocarpus tetragonolobus* (L.) DC) seeds"; *Plant Food for Human Nutrition*, 1987, vol. 36, p. 367 Abstract.

Prakash et al., "Amino acid profile of winged bean (*Psophocarpus tetragonolobus* (L.)DC): a rich source of vegetable protein", *Plant Foods for Human Nutrition*, 1987, vol. 37, p. 261 Abstract.

Prakash et al., "Variation in Protein and Trypsin Inhibitor Activity with Maturity and Amino Acid Composition of Winged Bean (*Psophocarpus tetragonolobus*) Seeds", *J Sci Food Agric*, 1991, vol. 57, p. 623 Abstract.

Asparagus Adscendens Boxb., *CRC Handbook of Ayurvedic Medicinal Plants*, CRC Press, Inc., 1990, p. 55.

Asparagus adscendent Roxb. (*Liliaceae*); *A Lexicon of Medicianl Plants in India*, vol. 1, 1999, p. 203.

Asparagus Linn, A. Adscendens Roxb., *The Wealth of India: A Dictionary of Indian Raw Materials & Industrial Products*, National Institute of Science Communication; Council of Scientific & Industrial *Research, Pusa, New Delhi 110–012*, vol. I, 1948 pp 131–132.

*Asparagus racemosus* Willd., *CRC Handbook of Ayurvedic Medicinal Plants*, CRC Press Inc., 1990, p. 56.

*Asparagus racemosus* Willd. Var. javanicus Baker (*Liliaceae*), *A Lexicon of Medicinal Plants in India*, 1999, vol. 1, p. 205.

A. *racemosus* Willd, *The Wealth of India: A Dictionary of Indian Raw Materials & Industrial Products*, National Institute of Science Communication; Counsel of Scientific & Industrial Research, Pusa, New Delhi, India 110–102; CSIR, 2000, p. 132.

*Boerhaavia diffusa* Linn, *CRC Handbook of Ayurvedic Medicinal Plants*, CRC Press Inc., 1990, p. 79.

Boerhaavia, *A Lexicon of Medicinal Plants in India*, 1999, vol. 1, p. 297.

*Centella asiatica* (Linn.), *CRC Handbook of Ayurvedic Medicinal Plants*, CRC Press, Inc., 1990, vol. 1, p. 208.

*Centella asiatic* (L.) Urban (*Apiaceae*), *A Lexicon of Medicinal Plants in India*, 1999, vol. 1, p. 413.

*Centipida minima* (L.) A. Br. et Aschers (*Asteraceae*), *A Lexicon of Medicinal Plants in India*, 1999, vol. 1, p. 414, 428–430.

Myristica Frangans Houtt, *CRC Handbook of Ayurvedic Medicinal Plants*, CRC Press Inc., 1990, vol. 1 p. 238.

Piper Longum Linn, *CRC Handbook of Ayurvedic Medicinal Plants*, CRC Press, Inc., 1990, vol. 1, p. 264.

Piper Longum Linn, *The Wealth of India: A Dictionary of Indian Raw Materials & Industrial Products*, National Institute of Science Communication; Counsel of Scientific & Industrial Research, Pusa, New Delhi, India 110–102; vol. 8, 1969, p. 96.

*Sida cordifolia* Linn., *CRC Handbook of Ayurvedic Medicinal Plants*, CRC Press, Inc., 1990, vol. 1, p. 303.

*Sida cordifolia* Linn, *The Wealth of India: A Dictionary of Indian Raw Materials & Industrial Products*, National Institute of Science Communication; Council of Scientific & Industrial Research, Pusa, New Delhi, India 110–012, vol. 9, 1972, pp. 323–324.

*Saraca indica* Linn., *CRC Handbook of Ayurvedic Medicinal Plants*, CRC Press Inc. 1990, p. 298.

*Sacara asoca*, *The Wealth of India: A Dictionary of Indian Raw Materials & Industrial Products*, National Institute of Science Communication; Council of Scientific & Industrial Research, Pusa, New Delhi, India 110–012, 2000, pp. 233–234.

*Withania somnifera* Dumal, *CRC Handbook Ayurvedic Medicinal Plants*, CRC Press, Inc., 1990, p. 337.

W. *somnifera* Dunal, The Wealth of India: A Dictionary of Indian Raw Materials & Industrial Products; National Institute of Science Communication; Council of Scientific & Industrial Research, Pusa, New Delhi, India 110–012, 1976, vol. 10, pp. 581; 585.

Mucuma, *The Wealth of India: A Dictionary of Indian Raw Materials & Industrial Products*; National Institute of Science Communication; Council of Scientific & Industrial Research, Pusa, New Delhi, India 110–012, CSIR, vol. 6, pp 442–443.

Prakash et al., "Some nutritional properties of the seeds of three Mucuna species", *International Journal of Food Sciences and Nutrition*, 2001, vol. 52, p. 79 Abstract.

Boehaavia Linn, *The Wealth of India: A Dictionary of Indian Raw Materials & Industrial Products*, National Institute of Science Communications; Council of Scientific & Industrial Research, Pusa, New Delhi, India 110–012, 1990, vol. 1, p. 199.

CUSTOM MADE HERBAL HEALTH PROMOTIVE FORMULATION FOR FEMALES/EXPECTANT MOTHERS

FIELD OF THE INVENTION

The present invention relates to an herbal health protective and promotive nutraceutical formulations for females/expectant mothers.

BACKGROUND OF THE INVENTION

Nutraceuticals, are foods or bioactive ingredients in foods that protect or promote health whether delivered in raw agricultural commodities, processed foods, dietary supplements, extracts, beverages or other products and occurs at the intersection of food and pharmaceutical industries. The development of next generation nutraceutical "super foods" or products consisting value-addition in the traditional natural diets. Their ingredients have tremendous impact on the health care system and may provide medical health benefits including the prevention and or treatment of diseases. Nutraceuticals have potential to be used as food supplement, preventive medicine and the growing evidence points in the direction that certain foods fight and or prevent against diseases.

The food may be nutraceutical i.e. a food or parts of food that provide medical health benefits including the prevention and or treatment of diseases. Functional foods provide specific benefits, and medical foods developed for use under medical supervision to treat or manage particular disease or nutritional deficiency stage. Nutraceutical and functional-foods are a hybrid of both the traditionally defined food and drug arenas. The word Nutraceuticals combines 'nutrition' and 'pharmaceuticals' to mean that food can be used as preventive drugs or food supplements. The entire concept is based on the disease preventing phytonutrients present in foodstuffs of the diet in combating diseases. The major phytonutrients identified to have nutraceutical properties include terpenes, phytosterols, phenols and theols. Carotenoids found in green leafy vegetables like amaranth, Chenopodium (goose foot), mustard, 'Methi', spinach and cabbage etc are precursor of vitamin A. They have preventive action against many eye diseases, cancer and also acts as antioxidant. Limonoids also acts as antioxidants by protecting lung tissues from oxygen free radicals. Antioxidants have been associated with reduced risk of cardiovascular diseases and several types of cancer. They are known to act to defuse the volatile toxic molecules of free oxygen radicals, a by-product of cell metabolism. These are also produced in the body on exposure to sunlight, X-rays, ozone, tobacco smoke, auto-exhaust and other environmental pollutants. Carotenoids, tocopherols, ascorbates and polyphenols are strong natural antioxidants generally found in plants and foods. They enhance the body's detoxification activity and protect against certain type of cancers by eliminating ill health causing chemical from the body to prevent degenerative diseases. Phytosterols competes with dietary cholesterol for uptake in intestine thereby blocking cholesterol absorption into the body and can also prevent the development of tumor in breast and prostate glands. Phenols a large group of phytonutrients, with sub classes in flavonoids, biflavonoids, anthocyanines and isoflavonoids have profound importance in preventive medicine. Berries, grapes and eggplants are rich in phenolics and have protective action against oxidative damage of tissues and inflammation. It has been proved that phytochemicals can enhance the efficacy of vitamin C, can also act against allergies, ulcers, tumors, platelet aggregation, controlling hypertension and can reduce the risk of estrogen induced cancer. Anthocyanidines or flavonals have significant role in collagen protein synthesis and are important in sports medicine. Beans and other legumes are rich natural sources of protein with the necessary nutrients needed for a healthy body and many of them contain specific immune-boosting potential.

Theols are major sulfur containing phytonutrients and the nutraceutical foods rich in theols include garlic, onion, mustard, cabbage, turnip and chives. They are potent antimutagenic and anticarcinogenic agents and gives cardio vascular protection. Cruciferous vegetables are rich source of glucosinolates, which activate liver detoxification enzymes and can reduce tumor. They can also block the activity of toxins produced by bacteria and viruses thereby building immunity against diseases. Indoles found in citrus and gooseberries are effective against carcinogenic chemicals in the intestine. The herbs like alfalfa, *Ginko biloba*, Ginseng, St John's wort etc are considered to be good for brain development. Asparagus acts as immunomodulator, builds healthy capillary, RBC, stimulate kidney and protects liver.

Malnutrition is a major problem in the developing and third world countries resulting several diseases and low IQ in children. A child's capacity to learn is directly related to food intake and good nutrition (Child Nutrition Advisory Council, USA). The development of brain mainly depends on the health of pregnant and lactating mother finally on the quality of mother's diet. Similarly, the food also plays significant role in the general health of infants, growing children, diabetics, heart, nerves and aged. The right foods do have the power to heal, keeping good health of body functions, ageing, rejuvenating, immuno-modulating and prevention against diseases, just as the wrong foods can cause sickness, rapid ageing and premature death. The environmental and dietary factors i.e. poor nutrition habits are one of the co-factors for different diseases. To combat malnutrition and growing demand of nutraceuticals need tailoring practices through value addition to optimize the concentration and bioavailability of the desired food components.

PRIOR ART REFERENCES

Reference is made to a book by Balch P A & Balch J F (Rx Prescription for Dietary Wellness, 1993, USA) wherein important isoflavones, genestin and diazin found in soybean (*Glycine max*) have properties against tumor growth, protease inhibitors found in legumes, can block natural carcinogens from forming tumors. Whole grains, germinated seeds, legumes and herbs are basically powerful foods. Reference is made to books by Guha Bakshi D N, Sensarma P & Pal D C (A Lexicon of Medicinal Plants in India, Naya Prokash, 1999, Calcutta, India); Chopra R N, Nayar S L, & Chopra I C (Glossary of Indian Medicinal Plants, NISCOM, CSIR, New Delhi, India 1999); Anonymous (Wealth of India, Raw Materials, CSIR, New Delhi, India) and a chapter Seed Proteins by Prakash D (Current Concepts in Seed Biology K G Mukerji et al. eds 1993); published research articles by Misra P S, Prakash D, Pandey R M & Pal M, Fitoterapia 56: 318–320, 1985; Prakash D, Narayan P & Misra P S, Plant Foods Hum. Nutr. 36: 341–344, 1987; Prakash D, Misra P N & Misra P S, J. Sci. Food Agric. 57: 623–626, 1991; Prakash D & Pal M, J. Sci. Food Agric. 58: 145–147, 1992; Prakash D, Nath P & Pal M, J. Sci. Food Agric. 62: 203–205, 1993; Prakash D, Joshi B D & Pal M, Int. J. Food Sci. Nutr. 46: 47–51, 1995; Prakash D & Pal M, Int. J. Food Sci. Nutr.

49: 271–275, 1998; Prakash D & Pal M, Int. J. Food Sci. Nutr. 49: 285–288, 1998; Prakash D, Niranjan A & Tewari S K Int. J. Food Sci. Nutr. 52: 79–82, 2001) wherein the significant nutritional composition and pharmaceutical uses of soybean (*Glycine max*), kidney-bean (*Phaseolus vulgaris*), chick-pea (*Cicer arietinum*), black-gram/'Urd' (*Phaseolus mungo*), green-gram/'Mung' (*Phaseolus radiatus*), winged bean (*Psophocarpus tetragonolobus*), 'Kewanch' (*Mucuna pruriens*), wheat (*Triticum aestivum*) barley (*Hordeum vulgare*), amaranth (*Amaranthus hypochondriacus*), goose foot/quinoa (*Chenopodium quinoa*) and buckwheat (*Fagopyrum esculantus*) have been described. These seeds are being used as edible foods in the form of different kind of preparations without fortification with herbs/medicinal plants. Reference is made to books by Guha Bakshi D N, Sensarma P & Pal D C (A Lexicon of Medicinal Plants in India, Naya Prokash, 1999, Calcutta, India); Chopra R N, Nayar S L, & Chopra I C (Glossary of Indian Medicinal Plants, NISCOM, CSIR, New Delhi, India 1999); Kapoor L D (Handbook of Ayurvedic Medicinal Plants, CRC Press, Florida, 1990); Sharma P V (Dravyaguna Vijnana, Vol II, 1992, Chaukhambha Bharati Academy, Varanasi); Balch P A & Balch J F (Rx Prescription for Dietary Wellness, 1993, USA) and Anonymous (Wealth of India, Raw Materials, CSIR, New Delhi, India) wherein the traditional and modem medicinal uses of the herbs/medicinal plants like *Centella asiatica*, for brain development; *Asparagus racemosus* and *Chlorophytum tuberosum* as immuno-modulator, potent diuretic, galactogogue, aphrodisiac, protects against cancer, builds healthy capillary, RBC, stimulate kidney and liver; *Withania somnifera* as tonic, alterative, astringent, aphrodisiac; *Boerhaavia diffusa*, diuretic, hepatoprotective; *Saraca indica*, diuretic, gynecological disorders; *Sida cordifolia*, gonorrhea, antifetique; *Pueraria tuberosa*, diuretic, cardiotonic; *Piper longum*, cardiac stimulant, rejuvenator, bioavailability enhancer; *Elettaria cardamomum*, stimulant, stomachic, carminative, diuretic and *Myristica fragrans* as stimulant have been mentioned. These herbs/medicinal plants are being used for the preparation of different kind of medicines alone or in different combinations.

However, a number of patents have been granted on nutraceuticals, which comprises either a single or a mixture of several phytonutrients in concentrated form. In some cases, the products were fortified with synthetic ingredients also. Reference is made to patents (Patent No. AU2557899; WO9935917) wherein methods of infusing phytochemicals, nutraceuticals and other compositions into food products e.g. juices, fruits, vegetables and meats, etc through osmotic dehydration are described. The methods are tedious including the use of some chemicals during the preparation. Reference is made to patents (Patent No. AU4777100; WO0064282) wherein nutraceuticals and ingredients for functional foods are prepared by co-spray drying using fructans, fructooligosaccharides instead of maltodextrins as a drying agent and ingredients such as flavonoids, anthocyanins, resveratrol. The main emphasis has been limited to phenolic phytochemicals and products are in the form of a gel or cream, showing fat like texture which can only be used as spreader. Reference is made to patents (Patent No. AU4038800; WO0057726) wherein nutraceuticals comprising a blend of N-[N-(3,3-dimethylbutyl)-L-alpha-aspartyl]-L-phenylalanine 1-methyl ester (neotame) with another sweetener has been mentioned. The compounds used are synthetic and have limited importance only as sweetener or flavor modifier in nutraceuticals. Neotame is a synthetic variation of aspartame and poses potential major health problems like incidents of grand mal seizures, brain tumors and environmental hazards. Reference is made to patents (Patent Nos. U.S. Pat. No. 6,087,353; AU3696599; WO9959421) wherein esterified and subsequently hydrogenated phytosterol composition for use alone or for incorporation into foods, beverages, pharmaceuticals and nutraceuticals have been described. The isolated phytosterols from plants have been modified by chemical process of esterification for the physical characteristics. Reference is made to patent (U.S. Pat. No. 6,099,867) wherein a nutraceutical composition comprising water insoluble or water soluble antler powder or a combination and method of producing the same has been described. The products are non-ecofriendly of animal origin with limited nutraceutical importance. The nutracuticals with branded name as Dieter's Formula, Digestive Formula, Mega Man, Stress formula, vegetative Laxative, Memory helper with *Ginko biloba*, Revitalizer with Ginseng, Dieter's helper etc are available in international market (Internet). Like-wise in Indian market commercial products like Complan, Boost, Horlics, Bounrvita, Cerelac, Protinex, Body Pro, Mega Mass, Muscle Builder, 90 Plus Protein and Soyatein etc are available. Besides the natural ingredients majority of the products also contain some synthetic amino acids, vitamins and other ingredients. Most of them are without any natural herbs/medicinal plants and recommended as food supplement for nutrition. While, the present invention provides a process for the preparation of nutraceuticals with specific combination of edible legumes, cereals, pseudocereals for natural nutrients and herbs/medicinal plants with significant medicinal values to provide optimum balanced nutrition and general health protective, preventive and promotive benefits. To the best of our knowledge any process for nutraceutical preparation does not exist comprising a combination of legumes, cereals, pseudocereals fortified with herbs/medicinal plants used in the present investigation. A literature survey and internet screening revealed that nutraceuticals comprising a proper combination of natural edible seeds, herbs and medicinal plants has not yet been prepared to provide adequate nutrition and health protective benefits.

OBJECTS OF THE INVENTION

The main object of the present invention relates to the custom made tailored nutraceutical functional food composition(s), in a proper combination of natural edible seeds, herbs/medicinal plants to provide optimum nutrition, health protective, preventive and promotive benefits for general health care of the females, pregnant and lactating mothers and to ward off malnutrition.

Another object of the present invention is to provide an herbal health protective nutraceutical formulation, which obviates the drawbacks as detailed above.

Another object of the present invention is to formulate a combination of edible legumes, cereals, pseudocereals with promising potential for the development of base material to provide essential natural nutrients.

Still another object of the present invention is to develop health protective and preventive nutraceutical formulation as food supplements with specific functional attributes by fortifying nutritional base material with herbs/medicinal plants.

Yet another object of the present invention is to provide nutraceutical formulation for optimum nutrition, general health promotive and well being of the females to ameliorate the general health at prenatal and post natal stages and to ward off malnutrition.

SUMMARY OF THE INVENTION

The present invention relates to the custom made tailored nutraceutical functional food composition(s), in a proper combination of natural edible seeds, herbs/medicinal plants to provide optimum nutrition, health protective, preventive and promotive benefits for general health care of the women, , pregnant and lactating mothers and to ward off malnutrition.

DETAILED DESCRIPTION

Accordingly, the present invention provides a herbal health protective, promotive neutraceutical formulation for women/expectant human mothers, said formulation comprising seeds/seed products selected from the group consisting of legumes, cereals and pseudocereals ranging from 80–90% and an extract ranging between 10–20%.

Also, the present invention provides a composition used as a herbal health protective, promotive neutraceutical formulation for females/expectant mothers, said composition comprising the said formulation consisting of seed powder mixture herbs/medicinal plant extract, and the composition further comprising sugar/jaggary , milk powder, *Piper longum* fruits, *Myristica fragrans* fruit powder, *Elettaria cardamomum* seed powder and coca powder.

The present invention also provide a process for the preparation of custom made herbal health protective, promotive nutraceutical formulations which may be used as food supplements to ameliorate the general health of females with optimum nutrients so as to ensure the optimal growth and development of the child both at prenatal and post natal stages.

The process comprises the seeds, from selected genera of Glycine, Phaseolus, Cicer, Psophocarpus, Mucuna, Triticum, Hordeum, Amaranthus, Chenopodium and Fagopyrum, may be roasted by keeping in microwave oven (BPL-Sanyo, model BMO 800 TS, frequency 2450 Mhz) ranging from 2 to 15 minutes separately, the microwave roasted seeds, 12 in number, may be powdered separately to pass through a sieve ranging from 50 to 400-mesh, the seed powders may be mixed ranging from 0 to 75% to get the base products, in a mixer grinder ranging from 5 to 55 minutes and may be called as base product, the roots, fruits, bark, whole plant of natural authentic herbs/medicinal plants from the genera of Centella, Withania, Pueraria, Asparagus, Chlorophytum, Boerhaavia, Sida, Saraca, Piper, Elettaria and Myristica may be collected from different natural sources in India and may be cut into small pieces 2–10 cm, dried under shade ranging from 25 to 45° C., crushed and powdered ranging from 10 to 20-mesh separately, the powdered roots, fruits, bark, whole plant of natural authentic herbs/medicinal plants may be mixed ranging from 0 to 50% and may be extracted with aqueous alcohol mixture ranging from 10 to 90% v/v thrice for a period ranging from 12 to 48 hours, the alcohol may be selected from a group of methanol, ethanol, propanol and butanol, at temperature ranging from 25 to 45° C., the solvent from combined extractives may be removed under reduced pressure ranging from 20 to 100 psi at a temperature ranging from 35 to 65° C. and the viscous residue thus obtained may be called as the plants extract, the residue may be suspended in water in the ratio ranging from 20 to 70% and mixed with mixer grinder for a period ranging from 10 to 50 minutes, the suspension of plants extract may be mixed with the mixture of roasted seed powders ranging in the ratio from 0.4 to 20% and mixed thoroughly for a period of ranging from 10 to 50 minutes, the plants extract and seed powders mixture may be dried for a period ranging from 12 to 48 hours at a temperature ranging from 30 to 50° C., the dried plants extract and seed powders mixture may be again mixed thoroughly in a mixer grinder for a period of ranging from 5 to 50 minutes, to get the final nutraceutical products in the mixture of base product and plants extract, some additional ingredients like pale sugar powder in the ratio ranging from 0 to 50%, jaggary in the ratio ranging from 0 to 50%, milk powder in the ratio ranging from 0 to 30%, coca powder in the ratio ranging from 0 to 15%, *Elettaria cardamomum* (Elaichi) powder in the ratio ranging from 0 to 8%, *Piper longum* (Pippali) fruit powder ranging from 0–5%, *Myristica fragrans* (Jaiphal) fruit powder ranging from 0–5%, may also be added, the total mixture thus obtained may be mixed thoroughly in a mixer grinder for a period of ranging from 5 to 50 minutes to get the nutraceuticals. The end product may be used in the form of powder, granules, biscuits, tablet or capsule etc.

It was observed that the seeds from the genera of Glycine, Phaseolus and Cicer are essential, Triticum, Hordium and Amaranthus additional, Psophocarpus, Mucuna, Fagopyrum and Chenopodium are optional components of the base material. Among the herbs/medicinal plants from the genera of Centella, Chlorophytum, Boerhaavia and Sida are essential, Withania, Pueraria, Asparagus, Saraca additional, Piper, Elettaria and Myristica are optional components of the value addition plant material. The combination of the present nutraceuticals is not a mere admixture of the ingredients used resulting in aggregation of their properties but a mixture having synergistically enhanced properties useful as food supplement for health protective, preventive and promotive benefits of the females, pregnant and lactating mothers including pre and post natal stages.

Embodiments

In an embodiment of the provides a herbal health protective, promotive and nutraceutical formulation for women, human expectant mothers, wherein the said formulation comprising seeds/seed products selected from the group consisting of legumes, cereals and pseudocereals ranging from 80–90% by wt; 10–20% by wt of extract obtained from essential herbs/medicinal plants of the genera Centella, Chlorophytum, Boerhaavia and Sida, and optional herbs/medicinal plants selected from the *Withania somnifera, Pueraria tuberosa, Asparagus racemosus* and *Saraca indica*.

In another embodiment of the invention, the seeds/seed products are selected from dried seeds, roasted seeds and powdered seeds.

In another embodiment of the invention, the legumes used are essentially selected from the group comprising *Glycine max, Cicer arietinum, Phaseolus mungo, Phaseolus vulgaris* and *Phaseolus radiatus*, and optionally selected from the group comprising *Psophocarpus tetragonolobus* and Mucunapruriens.

In still another embodiment of the invention relates to the total amount of legumes used in the formulation is ranging from 55–60% by wt.

Yet another embodiment of the invention, the cereals used are selected from *Triticum aestivum, Hordeum vulgare* or mixtures thereof.

Yet another embodiment of the invention, the pseudocereals used are selected from *Amaranthus hypochondriacus, Fagopyrum esculantus, Chenopodium quinoa* or mixtures thereof.

Yet another embodiment of the invention, the total amount of cereals used is in the range between 15–25% by wt.

Yet another embodiment of the invention, the total amount of pseudocereal used is in the range between 20–30% by wt.

Yet another embodiment of the invention, the said herbs/medicinal plant parts used is selected from roots, fruits, bark and whole plants.

Yet another embodiment of the invention, the total amount of herbs/medicinal plants used is X, wherein X is ranging between 10–20% by wt of the formulation.

Yet another embodiment of the invention relates to the amounts of the essential herbs/medicinal plants namely *Centella asiatica, Chlorophytum tuberosum, Boerhaavia diffusa* and *Sida cordifolia* are used in the ranges between 10–40% by wt of X, 2–20% by wt of X, 5–30% by wt of X and 10–20% by wt of X respectively.

Yet another embodiment of the invention, the amounts of the essential herbs/medicinal plants namely *Centella asiatica, Chlorophytum tuberosum, Boerhaavia diffusa* and *Sida cordifolia* are used in the ranges between 16–32% by wt of X, 4–16% by wt of X, 5–24% by wt of X and 12–16% by wt of X respectively.

Yet another embodiment of the invention, the amount of the optional herbs/medicinal plants namely *Withania somnifera, Pueraria tuberosa, Asparagus racemosus* and *Saraca indica* are used in the ranges between 0–16% by wt of X, 0–24% by wt of X and 0–16% by wt of X and 0–12% by wt of X respectively.

Yet another embodiment of the invention, the said herbal formulation optionally contains acceptable amount of further additives selected from Piper, Elettaria and Myristica.

One more embodiment of the invention relates to a herbal health protective, promotive and nutraceutical composition for females and expectant mothers, wherein the said formulation comprising of seed powder mixture ranging from 44 to 52%, herbs/medicinal plant extract ranging from 5 to 13%, sugar/jaggary ranging form 20 to 35%, milk powder ranging from 0 to 20%, *Piper longum* fruit powder ranging from 0.5 to 5.0%, *Myristica fragrans* fruit powder ranging from 0 to 5.0%, *Elettaria cardamomum* seed powder ranging from 0 to 4.0%, coca powder ranging from 0 to 10%.

In yet another embodiment of the invention, the seed powder mixture contain legumes in the range between 23–31%, cereals in the range between 6–17% and psuedocereals in the range between 10–13%.

In yet another embodiment of the invention, the end-product is suitable for use in the form of powder, granules, biscuits, tablets, capsules or any other suitable forms.

One more embodiment of the invention relates to a process for the preparation of herbal health protective, promotive nutraceutical compositions useful as food supplements to ameliorate the general health of females/expectant mothers with optimum nutrients so as to ensure the optimal growth and development of the child both at pre-natal and post-natal stages, said process comprising a. selecting one or more seeds/seed products from the group consisting of legumes, cereals and pseudocerels wherein, the legumes consisting plants of genera Glycine, Cicer, Phaseolus, Psophocarpus, Mucuna, *P. vulgaris*, and *P. radiatus*, cereals consisting plants of genera Triticum and Hordeum, and, pseudocereals consisting plants of genera Amaranthus Chenopodium and Fagopyrum, b. roasting the seeds/seed products for 2 to 15 minutes under microwave conditions having frequency 1500–2500 Mhz, c. powdering the roasted seeds to a mesh size of 50–400 and mixing the same to obtain a base product, d. obtaining extract of herbs/medicinal plants from one or more plants of genera Centella, Withania, Pueraria, Asparagus, Chlorophytum, Boerhaavia, Sida and Saraca, and drying the extract to obtain a residue, and e. mixing the plants extract residue with the base product obtained from step (c) to get the final nutraceutical products and optionally adding one or more additives selected from sugar, jaggary, milk powder, *Piper longum, Myristica fragrants, Elettaria cardamomun* and coca powder.

In another embodiment of the invention, the roasted seed powders are mixed in various proportions ranging up to 80% and the plant parts used are selected from roots, fruits, bark and whole plant of herbs/medicinal plants ranging up to 20% are selected for use in the nutraceutical products.

In another embodiment of the invention, the herbs/medicinal plants are cut into small pieces ranging from 2 to 10 cm, dried under shade at the temperature ranging from 25 to 45° C. and crushed to coarse powder ranging from 10 to 20 mesh size before extraction and the crushed and powdered herbs/medicinal plants are mixed up to 50% of the total mixture.

In yet another embodiment of the invention, the powdered herbs/medicinal plants mixture is extracted with aqueous alcohol in the range of 10 to 90% v/v thrice for 12 to 48 hours, at temperature ranging from 25 to 45° C.

In yet another embodiment of the invention, the alcohol is selected from methanol, ethanol, propanol and butanol.

In yet another embodiment of the invention, the said solvent from combined extracts is removed under reduced pressure ranging from 20 to 100 PSI at temperature ranging from 35 to 65° C. and the viscous residue thus obtained is called as plants extract, the plants extract is suspended in water in the ratio ranging from 20 to 70% by stirring for 10 to 50 minutes and is mixed with roasted seed powder mixture in the ratio ranging up to 20%.

In yet another embodiment of the invention, the mixture of plants extract and roasted seed powders are mixed thoroughly in a mixer grinder for a period of ranging from 5 to 50 minutes and the mixture is dried for a period of ranging from 12 to 48 hours at temperature ranging from 30 to 50° C.

In yet another embodiment of the invention, the dried plants extract and seed powders mixture is again mixed thoroughly in a mixer grinder for a period of ranging from 5 to 50 minutes and the powder thus obtained is used to prepare final nutraceuticals.

In yet another embodiment of the invention, the amount of optional additives used namely sugar/jaggary or mixture thereof, milk powder, *Piper longum, Myristica fragrants, Elettaria cardamomun* and coca powder are in the ranges between 23–50% by wt, 0–30% by wt, 0.5–5% by wt, 0–5% by wt, 0–8% by wt and 1–15% by wt respectively.

In yet another embodiment of the invention, the optional additives present are in the ranges between sugar/jaggary 20–35% by wt, milk powder 0–20% by wt, *Piper longum* 0.5–5% by wt, *Myristica fragrants* 0–3% by wt, *Elettaria cardamomun* 0–4% by wt and coca powder 0–10% by wt.

In yet another embodiment, the dried, powdered, mixture of plants extract, roasted seed powders, sugar/jaggary, milk powder, coca powder, *Elettaria cardamomum* powder, *Piper longum* fruit powder and *Myristica fragrans* (Jaiphal) fruit powder mixture is mixed thoroughly in a mixer grinder for a period of ranging from 5 to 50 minutes to get the final nutraceuticals.

In yet another embodiment the nutraceutical formulations, as herein described for the composition, methodology, preparation of base materials and value addition by plants extract to get the end products, may be used as health protective, promotive, food supplements to ameliorate the general health of females with optimum nutrients so as to ensure the optimal growth and development of the child both at prenatal and post natal stages.

Novelty

The novelty of present invention is the specific combination of legumes, cereals, pseudocereals fortified with herbs/medicinal plants and the process for the preparation of nutraceuticals. The nutraceuticals are with optimum nutrition, non toxic, natural herbal plant products, easy to digest, have protective, preventive and health promotive properties for the best health and vigour of the females, pregnant and lactating mothers so as to ensure the optimal growth and development of the child both at prenatal and post natal stages.

The present invention provides a process for the preparation of custom-made herbal health protective nutraceuticals.

The present invention provides formulation for the combination of edible legumes, cereals, pseudocereals with promising potential for the development of well balanced nutritional base material.

The present invention provides value added products with synergistic health promotive, protective and preventive effects of natural herbs/medicinal plants to get specifically designed nutraceuticals for well balanced natural nutrients, to get optimum nutrition for general health protective benefits to the females, pregnant and lactating mothers and to ward off malnutrition.

The invention is described with reference to the examples, which are provided by way of illustration only, and these examples should not be construed to limit the scope of the present invention.

EXAMPLES

Specific Combinations

To prepare nutraceutical formulation the seeds of *Glycine max, Cicer arietinum, Phaseolus mungo, Triticum aestivum, Hordeum vulgare, Amaranthus hypochondriacus* and *Fagopyrum esculantus* were roasted by keeping in microwave oven for 3 minutes separately. The microwave roasted seeds, were powdered separately to pass through a 100-mesh sieve. The seed powders and herbs/medicinal plants extract were mixed as given in example 1.

Example 1

The microwave roasted seed powders of *Glycine max* 30 g, *Cicer arietinum* 15 g, *Phaseolus mungo* 10 g, *Triticum aestivum* 10 g, *Hordeum vulgare* 10 g, *Amaranthus hypochondriacus* 15 g and *Fagopyrum esculantus* 10 g were mixed for 20 minutes in a mixer grinder. The roots, fruits, bark, whole plant of natural authentic herbs/medicinal plants collected from different natural sources in India were cut into small pieces of about 3 cm, dried under shade at 25° C., crushed and powdered to 10-mesh. The dried powder of *Centella asiatica* (Brahmi) whole plant 250 g, *Withania somnifera* (Ashwagandha) roots 50 g, *Pueraria tuberosa* (Vidhari) roots 50 g, *Asparagus racemosus* (Satawari) roots 50 g, *Chlorophytum tuberosum* (Safed musli) roots 50 g, *Boerhaavia diffusa* (Punarnava) roots 150 g, *Sida cordifolia* (Bala) roots 100 g and *Saraca indica* (Ashoka) bark 100 g were extracted with 1.2 lit of aqueous alcohol 40% v/v thrice for 24 hours, at temperature 30° C., the solvent from combined extractives was removed under reduced pressure at 25 psi, at temperature of 50° C. and the viscous residue thus obtained was called as the plants extract. The 10 g of plants extract was suspended in 20 ml water and mixed with mixer grinder for a period of 30 minutes, the suspension of plants extract was mixed with the 90 g mixture of roasted seed powders and mixed thoroughly for a period of 30 minutes. The plants extract and seed powders mixture was dried for 42 hours at 40° C., the dried plants extract and seed powders mixture was again mixed thoroughly in a mixer grinder for 25 minutes. The powder thus obtained was used to prepare final nutraceuticals. The 53.0 g dried plants extract and seed powders mixture was mixed with 35.0 g pale sugar powder, 10.0 g milk powder, 0.5 g *Piper longum* (Pippali) fruit powder, 0.5 g *Myristica fragrans* (Jaiphal) fruit powder and 1.0 g *Elettaria cardamomum* (Elaichi) powder. The total mixture was mixed thoroughly in a mixer grinder for 25 minutes to get the final nutraceutical product.

The combination of the present nutraceuticals is a mixture having synergistic health protective and promotive properties useful as food supplement for females.

To prepare nutraceutical formulation the seeds of *Glycine max, Phaseolus vulgaris, Phaseolus radiatus, Psophocarpus tetragonolobus, Triticum aestivum, Amaranthus hypochondriacus* and *Chenopodium quinoa* were roasted by keeping in microwave oven for 7 minutes separately. The microwave roasted seeds, were powdered separately to pass through a 200-mesh sieve. The seed powders and herbs/medicinal plants extract were mixed as given in example 2.

Example 2

The microwave roasted seed powders of *Glycine max* 15 g, *Phaseolus vulgaris* 15 g, *Phaseolus radiatus* 20 g, *Psophocarpus tetragonolobus* 5 g, *Triticum aestivum* 15 g, *Amaranthus hypochondriacus* 25 g and *Chenopodium quinoa* 5 g were mixed for 30 minutes in a mixer grinder. The roots, whole plant, bark, fruits of natural authentic herbs/medicinal plants collected from different natural sources in India were cut into small pieces of about 3 cm, dried under shade at 30° C., crushed and powdered to 10-mesh. The dried powder of *Centella asiatica* (Brahmi) whole plant 200 g, *Withania somnifera* (Ashwagandha) roots 100 g, *Pueraria tuberosa* (Vidhari) roots 75 g, *Chlorophytum tuberosum* (Safed musli) roots 25 g, *Boerhaavia diffusa* (Punarnava) roots 100 g, *Sida cordifolia* (Bala) roots 75 g and *Saraca indica* (Ashoka) bark 50 g were mixed and extracted with 1.0 lit aqueous alcohol 60% v/v thrice for 32 hours, at a temperature of 35° C., the solvent from combined extractives was removed under reduced pressure at 40 psi, temperature of 60° C. and the viscous residue thus obtained was called as the plants extract. The 12 g of plants extract was suspended in 30 ml water and mixed with mixer grinder for a period of 30 minutes, the suspension of plants extract was mixed with the 88 g mixture of roasted seed powders and mixed thoroughly for a period of 35 minutes. The plants extract and seed powders mixture was dried for 36 hours at 45° C., the dried plants extract and seed powder mixtures were again mixed throughly in a mixer grinder 35 minutes. The powder thus obtained was used to prepare final nutraceuticals. The 50 g dried plants extract and seed powders mixture was mixed with 20 g jaggary, 20 g milk powder, 3.0 g *Piper longum* (Pippali) fruit powder and 3.0 g *Myristica fragrans* (Jaiphal) fruit powder, 4.0 g *Elettaria cardamomum* (Elaichi) powder and the total mixture was mixed thoroughly in a mixer grinder for 30 minutes to get the final nutraceuticals.

The combination of the legumes, cereals, pseudocereals and herbs/medicinal plants in the present investigation is a mixture having synergistic properties useful as food supplement for females, pregnant and lactating mothers for pre and post natal health protective and promotive benefits.

To prepare nutraceutical formulation the seeds of *Glycine max, Phaseolus radiatus, Mucuna pruriens, Hordeum*

*vulgare, Amaranthus hypochondriacus* and *Fagopyrum esculantus* were roasted by keeping in microwave oven for 10 minutes separately. The microwave roasted seeds were powdered separately to pass through a 300-mesh sieve. The seed powders and herbs/medicinal plants were mixed as given in example 3.

Example 3

The microwave roasted seed powders of *Glycine max* 40 g, *Phaseolus radiatus* 10 g, *Mucuna pruriens* 10 g, *Hordeum vulgare* 20 g, *Amaranthus hypochondriacus* 15 g, and *Fagopyrum esculantus* 5 g were mixed for 25 minutes in a mixer grinder. The roots, fruits, whole plant of natural authentic herbs/medicinal plants collected from different natural sources in India were cut into small pieces of about 6 cm, dried under shade at 40° C., crushed and powdered to 20-mesh. The dried powder of *Centella asiatica* (Brahmi) whole plant 100 g, *Pueraria tuberosa* (Vidhari) roots 150 g, *Chlorophytum tuberosum* (Safed musli) roots 50 g, *Boerhaavia diffusa* (Punarnava) roots 150 g, *Sida cordifolia* (Bala) roots 100 g and *Asparagus racemosus* (Satawari) roots 75 g were mixed and extracted with 1.5 lit aqueous alcohol 70% v/v thrice for 36 hours, at 55° C., the solvent from combined extractives was removed under reduced pressure at 50 psi, temperature of 50° C. and the viscous residue thus obtained was called as the plants extract. The 15 g of plants extract was suspended in 50 ml water and mixed with mixer grinder for a period of 35 minutes, the suspension of plants extract was mixed with the 85 g mixture of roasted seed powders and mixed thoroughly for a period of 40 minutes. The plants extract and seed powders mixture was dried for 28 hours at 50° C., the dried plants extract and seed powders mixture was again mixed thoroughly in a mixer grinder 45 minutes. The powder thus obtained was used to prepare final nutraceuticals. The 60 g dried plants extract and seed powders mixture was mixed with 30 g pale sugar powder powder, 6.0 g coca powder and 4.0 g *Piper longum* (Pippali) fruit powder. The total mixture was mixed thoroughly in a mixer grinder for 50 minutes to get the final nutraceuticals.

The combination of the legumes, cereals, pseudocereals and herbs/medicinal plants in the present investigation is a mixture having synergistic properties useful as food supplement for health protective and promotive benefits of the females.

To prepare nutraceutical formulation the seeds of *Phaseolus vulgaris, Cicer arietinum, Phaseolus mungo, Phaseolus radiatus, Hordeum vulgare, Amaranthus hypochondriacus* and *Fagopyrum esculantus* were roasted by keeping in microwave oven for 12 minutes separately. The microwave roasted seeds, were powdered separately to pass through a 400-mesh sieve. The seed powders and herbs/medicinal plants were mixed as given in example 4.

Example 4

The microwave roasted seed powders of *Phaseolus vulgaris* 20 g, *Cicer arietinum* 10 g, *Phaseolus mungo* 10 g, *Phaseolus radiatus* 15 g, *Hordeum vulgare* 25 g, *Amaranthus hypochondriacus* 10 g and *Fagopyrum esculantus* 10 g were mixed for 35 minutes in a mixer grinder. The whole plant, roots of natural authentic herbs/medicinal plants collected from different natural sources in India were cut into small pieces of about 7 cm, dried under shade at 40° C., crushed and powdered to 10-mesh. The dried powders of *Centella asiatica* (Brahmi) whole plant 150 g, *Withania somnifera* (Ashwagandha) roots 80 g, *Asparagus racemosus* (Satawari) roots 100 g, *Chlorophytum tuberosum* (Safed Musli) roots 100 g, *Pueraria tuberosa* (Vidhari) roots 70 g, *Boerhaavia diffusa* (Punamava) roots 30 g and *Sida cordifolia* (Bala) roots 100 g were mixed and extracted with 1.0 lit aqueous alcohol 90% v/v thrice for 36 hours, at a temperature of 40° C., the solvent from combined extractives was removed under reduced pressure at 40 psi, temperature of 55° C. and the viscous residue thus obtained called was the plants extract. The 20 g of plants extract was suspended in 60 ml water and mixed with mixer grinder for a period of 45 minutes, the suspension of plants extract was mixed with the 80 g mixture of roasted seed powders and mixed thoroughly for a period of 45 minutes. The plants extract and seed powders mixture was dried for 48 hours at 50° C., the dried plants extract and seed powders mixture was again mixed thoroughly in a mixer grinder for 35 minutes. The powder thus obtained was used to prepare final nutraceuticals. The 65.0 g dried herbs extract and seed powder mixture was mixed with 20 g jaggary, 5.0 g *Piper longum* (Pippali) fruit powder and 10.0 g coca powder and the total mixture was mixed thoroughly in a grinder mixture for 40 minutes to get the final nutraceuticals.

The combination of the present nutraceuticals have synergistic health protective and promotive properties useful as food supplement for females, pregnant and lactating mothers.

TABLE 1

The amount (% composition) of seed powders (legumes, cereals & pseudocereals) in the base products.

| | Example Nos | | | | |
|---|---|---|---|---|---|
| | 1 | 2 | 3 | 4 | Range |
| Legumes | | | | | |
| *Glycine max* | 30 | 15 | 40 | 0 | |
| *Cicer arietinum* | 15 | 0 | 0 | 10 | |
| *Phaseolus mungo* | 10 | 0 | 0 | 10 | |
| *P. vulgaris* | 0 | 15 | 0 | 20 | |
| *P. radiatus* | 0 | 20 | 10 | 15 | |
| *Psophocarpus tetragonolobus* | 0 | 5 | 0 | 0 | |
| *Mucuna pruriens* | 0 | 0 | 10 | 0 | |
| Total Amount of Legumes | 55% | 55% | 60% | 55% | 55–60% |
| Cereals | | | | | |
| *Triticum aestivum* | 10 | 15 | 0 | 0 | |
| *Hordeum vulgare* | 10 | 0 | 20 | 25 | |
| Total amount of cereals | 20% | 15% | 20% | 25% | 15–25% |
| Pseudo Cereals | | | | | |
| *Amaranthus hypochondriacus* | 15 | 25 | 15 | 10 | |
| *Fagopyrum esculantus* | 10 | 0 | 5 | 10 | |
| *Chenopodium quinoa* | 0 | 5 | 0 | 0 | |
| Total amount of pseudo Cereals | 25% | 30% | 20% | 20% | 20–30% |

TABLE 2

The amount (%) of different herbs/medicinal plants in the total used for extraction with alcohol.

| Herbs/Medicinal plants% | Example Nos | | | | Range |
|---|---|---|---|---|---|
| | 1 | 2 | 3 | 4 | |
| Essential | | | | | |
| Centella asiatica | 32 | 32 | 16 | 23 | 16–32% |
| Chlorophytum tuberosum | 6 | 4 | 8 | 16 | 4–16% |
| Boerhaavia difussa | 19 | 16 | 24 | 5 | 5–24% |
| Sida cordifolia | 12 | 12 | 16 | 16 | 12–16% |
| Optional | | | | | |
| Withania somnifera | 6 | 16 | 0 | 13 | 0–16% |
| Pueraria tuberosa | 7 | 12 | 24 | 11 | 7–24% |
| Asparagus racemosus | 6 | 0 | 12 | 16 | 0–16% |
| Saraca indica | 12 | 8 | 0 | 0 | 0–12% |

Additional

The additional herbs *Piper longum* 0–5%, *Elettaria cardamomum* 0–8% and *Myristica fragrans* 0–5% was added in the end products.

TABLE 3:

The percent composition & ratio of the seed powders and Herbs/Plants extract 10–20 g (10, 12, 15 and 20 g) of the extract was mixed with 80–90 g of the base products (90, 88, 85 and 80 g mixture of the seed powders in examples 1, 2, 3 and 4 respectively).

| Ingredients % | Example Nos | | | |
|---|---|---|---|---|
| | 1 | 2 | 3 | 4 |
| Seed Powders % | 90 | 88 | 85 | 80 |
| Plants extract % | 10 | 12 | 15 | 20 |
| Ratio | (9:1) | (7.3:1) | (5.6:1) | (4:1) |

TABLE 5:

Record of Clinical Trial & Feed Back from Volunteers after consuming the Herbal Health Protective and Promotive Nutraceuticals for Females / Expectant mothers 1. Age group: 20–50 years
2. Profession/Family background: House wife, business & service class
3. Taste & Flavor: satisfactory to excellent After one week, two week, one month

| Product | One Week | Two Week | One Month | Remark |
|---|---|---|---|---|
| 1 | NS | NS | NS | NS (10)* |
| 2 | NS | NS | NS | NS (10) |
| 3 | NS | NS | Satisfactory | NS (10) |
| 4 | Satisfactory | Good | Good | Good (5) |
| 5 | Good | Good | Very Good | Good (5) |
| 6** | Good | Very Good | Very Good | Very Good (6) |
| 7** | Good | Very Good | Very Good | Very Good (7) |
| 8** | Very Good | Very Good | Very Good | Very Good (8) |
| 9** | Very Good | Excellent | Excellent | Excellent (8) |

NS = Non significant effect, cannot say
*Number of women who remarked out of ten;
**The products generated as final products The word satisfactory, good, very good and excellent stands for the efficacy of the products as reported by volunteers after consuming the product like no side effects, no any kind of digestive problem, improvement in vigour, energetic, on general health conditions as protective, preventive, promotive benefits etc.

Product 1–9=Base (Seed powders mixture)+Extract of single plant or different combinations of herbs/medicinal plants

TABLE 4:

Percentage Composition of ingredients in final/end product

| Ingredients (%) | Example Nos. | | | | Preferred ranges | |
|---|---|---|---|---|---|---|
| | 1 | 2 | 3 | 4 | I | II |
| *Seed powders Mixture % | 47.7 | 44 | 51 | 52 | 44–52 (TABLE 1) | 40–60 |
| Herbs/Medicinal Plants Extract % | 5.3 | 6 | 9 | 13 | 5–13 (TABLE 2) | 5–20 |
| Sugar/jaggary % | 35 | 20 | 30 | 20 | 20–35 | 20–35 |
| Milk Powder % | 10 | 20 | 0 | 0 | 0–20 | 0–30 |
| Piper longum % | 0.5 | 3 | 4 | 5 | 0.5–5 | 0.5–5 |
| Myristica fragrans % | 0.5 | 3 | 0 | 0 | 0–3 | 0–5 |
| Elettaria cardamomum % | 1 | 4 | 0 | 0 | 0–4 | 0–8 |
| Coca powder % | 0 | 0 | 6 | 10 | 0–10 | 0–15 |

*Detailed % Composition of Seed powders Mixture % in the end product

| | Example No | | | | Range % |
|---|---|---|---|---|---|
| | 1 | 2 | 3 | 4 | |
| Legumes % | 26.2 | 24.2 | 30.6 | 28.6 | 23–31 |
| Cereals % | 9.5 | 6.6 | 10.2 | 13.0 | 7–13 |
| Pseudocereals % | 12.0 | 13.2 | 10.2 | 10.4 | 10–13 |

Nutrition Composition of Commercially Available Samples
1. BOURNVITA:

| Nutrients per 100 g of Bournvita | | %RDA | Function |
|---|---|---|---|
| Protein | 7 g | 40 | Helps to build muscle tissues |
| Vitamin A | 950 Mcg | 60 | Good vision |
| Vitamin C | 70 mg | 40 | Repair of tissues |
| Thiamine | 2.4 mg | 65 | Healthy Nervous system |
| Niacin | 33.5 mg | 54 | Releases energy from food |
| Pyridoxine | 3 mg | 35 | Helps to build immunity |
| Vitamin $B_{12}$ | 1.5 Mcg | 65 | Growth & Development |
| Foli Acid | 350 Mcg | 70 | Helps blood formation |
| Calcium | 155 mg | 100 | Stronger bones & teeth |
| Iron | 26 mg | 20 | Prevents anemia |
| Riboflavin | | 65 | Metabolism of food |

RDA = Recommended Dietary allowance as per "Nutritive value of Indian foods"

Ingredients:
Malt extract, Sugar, Coca powder, Milk solids, Liquid glucose, Vitamins, Minerals, Leavening agent (Leavening substance used to make dough ferment), Salt.
2. COMPLAN (Chocolate flavour):
Approximate composition/100 g; Energy value 444 K cal

| Protein | 20%; | Fat | 16%; | Carbohydrate | 55% |
|---|---|---|---|---|---|
| Choline | 65 mg; | Sodium | 400 mg; | Phosphorus | 780 mg; |
| Chloride | 500 mg; | Vitamin A | 1060 IU; | Vitamin C | 25 mg; |
| Vitamin D | 150 IU; | Vitamin E | 3 IU; | Vitamin K | 0.045 mg |
| Iron | 13.5 mg; | Niacin | 6 IU; | Ca-pantothenate | 3.0 mg |
| Folic acid | 75 Mcg | With Vitamin A, B, C, D & E | | | |

Ingredients: Skimmed milk, sugar, vegetable oil, permitted antioxidants, maltodextrin, caramel-beet root juice powder, added flavour, minerals & Vitamins (Heinz India Ltd New Delhi)
3. COMPLAN (Natural flavour): Complete planned food in a drink with 23 vital nutrients.
Approximate composition/100 g; Energy value 444 K cal

| Protein | 20%; | Fat | 16%; | Carbohydrate | 55% |
|---|---|---|---|---|---|
| Choline | 65 mg; | Sodium | 400 mg; | Phosphorus | 780 mg; |
| Chloride | 500 mg; | Potassium | 920 mg; | Iodine | 110 mcg; |
| Vitamin A | 1060 IU; | Vitamin $B_1$ | 0.45 mg; | Vitamin $B_2$ | 0.57 mg; |
| Vitamin $B_6$ | 0.76 mg; | Vitamin $B_{12}$ | 0.76 mg; | Vitamin C | 30 mg; |
| Vitamin D | 150 IU; | Vitamin E | 3 IU; | Vitamin K | 0.045 mg |
| Iron | 13.5 mg; | Niacin | 6 IU; | Ca-pantothenate | 3.0 mg |
| Folic acid | 75 Mcg; | With Vitamin A, B, C, D & E | | | |

Ingredients: Skimmed milk, sugar, vegetable oil, permitted antioxidants, maltodextrin, caramel-beet root juice powder, added flavour, minerals & Vitamins (Heinz India Ltd New Delhi)
4. PROTINEX:
Protein hydrolysate-16.8%; Sugar-9.3%; Malt Extract-3.2%; Ca-phosphate-400 mg; Choline-bitartrate 150 mg; Vitamin A 1600 IU; Vitamin C 25 mg; Vitamin $B_1$ 1.0 mg; Vitamin $B_2$ 1.37 mg; Vitamin $B_6$ 0.5 mg; Vitamin $D_3$ 100 IU; Vitamin E 5 IU; Vitamin $K_3$ 0.13 mg; Iron-gluconate 17 mg; Niacinamide 15 mg; Pantothenate 1.0 mg; Folicacid 50 Mcg; Biotin 10 mg
5. CERELAC:

| Protein | 15.5%; | Fat | 9.0%; | Carbohydrate | 68.9%; |
|---|---|---|---|---|---|
| Na | 200 mg; | K | 470 mg; | Ca | 470 mg; |
| Fibre | 1.4 g; | Ash | 2.7%; | Moisture | 2.5% |
| 419 K cal | | | | | |

Ingredients: Fatless milk solid, wheat flour, sucrose, edible vegetable oil, vitamins & minerals.
6. HORLICS:
Ingredients: Wheat flour, milk, barley malted, malt extract, sugar, vitamins & minerals, cardamom powder.
7. BODY:

| Protein | 35%; | Fat | 2.0%; |
|---|---|---|---|

Zinc, Vitamin A, B, C, D, E, niacin, phosphorus, iron, calcium tri-calcium
Ingredients: Soy protein isolate, malt extract, sugar, milk, malt, vitamins & minerals.
8. SOYATEIN:
Ingredients: Defatted Soya flour granules National Botanical Research Institute, Lucknow Record of Clinical Trial & Feed Back from Volunteers Nutraceuticals/Health Care Products 1. Product(s) Volunteered to take: Herbal Health Promotive Nutraceuticals for Females
2. Age group: 20–50 years
3. Number of Volunteers: 10 in each case
4. Profession/Family background: House wife, business & service class
5. Taste & Flavor: Satisfactory to excellent
6. Feeling after Consuming the Product (e.g. Refreshing, Energetic, Diuretic etc.):

| After one week, two week, one month | | | | |
|---|---|---|---|---|
| Product | One Week | Two Week | One Month | Remark |
| 1 | NS | NS | NS | NS (10)* |
| 2 | NS | NS | NS | NS (10) |

-continued

| | After one week, two week, one month | | | |
|---|---|---|---|---|
| Product | One Week | Two Week | One Month | Remark |
| 3 | NS | NS | Satisfactory | NS (10) |
| 4 | Satisfactory | Good | Good | Good (5) |
| 5 | Good | Good | Very Good | Good (5) |
| 6 | Good | Very Good | Very Good | Very Good (6) |
| 7 | Good | Very Good | Very Good | Very Good (7) |
| 8 | Very Good | Very Good | Very Good | Very Good (8) |
| 9 | Very Good | Excellent | Excellent | Excellent (8) |

•Number of women who remarked out of ten;
Product No
1. Base + Centella;
2. Base + Centella + Chlorophytum;
3. Base + Centella + Boerhaavia + Chlorophytum;
4. Base + Centella + Boerhaavia + Chlorophytum + Sida;
5. Base + Centella + Boerhaavia + Chlorophytum + Sida + Withania;
6. Base + Centella + Boerhaavia + Chlorophytum + Sida + Wihania + Pueraria;
7. Base + Centella + Boerhaavia + Chlorophytum + Sida + Withania + Pueraria + Asparagus;
8. Base + Centella + Boerhaavia + Chlorophytum + Sida + Withania + Pueraria + Asparagus;
9. Base + Centella + Boerhaavia + Chlorophytum + Sida + Withania + Pueraria + Asparagus.

7. Suggestions:
Improvement in solubility or suspension

What is claimed is:

1. A herbal health promotive formulation to improve the general health of women or pregnant women said formulation comprising:
    80–90% by wt of said herbal health formulation comprising seeds or a seed product, in which said seeds or seed products is a legume;
    10–20% by wt of said herbal health formulation comprising an extract, said extract obtained from herbs or medicinal plants of the genera *Centella, Chlorophytum, Boerhaavia,* and *Sida;*
    optionally one or more extracts of a herb or a medicinal plant selected from the group consisting of *Withania somnifera, Pueraria tuberose, Asparagus racemosus,* and *Saraca indica;*
    optionally milk powder;
    optionally jaggery;
    optionally coca powder;
    optionally sugar powder; and
    optionally one or more further additives selected from the group consisting of *Piper, Elettaria,* and *Myristica.*

2. A herbal formulation as claimed in claim 1, wherein seeds or seed products are selected from dried seeds, roasted seeds and powdered seeds.

3. A herbal formulation as claimed in claim 1, wherein the legume is *Glycine max.*

4. A herbal formulation as claimed in claim 1, wherein the total amount of legume used in the formulation is in the range from 55–60% by wt of the formulation.

5. A herbal formulation as claimed in claim 1, wherein said herbs or medicinal plants are selected from roots, fruits, bark, and whole plants.

6. A herbal formulation as claimed in claim 1, wherein the total amount of herbs or medicinal plants is X, wherein X ranges between 10–20% by wt of the formulation.

7. A herbal formulation as claimed in claim 6, wherein X comprises 10–40% by wt of *Centella aisatica,* 2–20% by wt of *Chlorophytum tuberosum,* 5–30% by wt of Boerhaavia diffusa, and 10–20% by wt of *Sida cordifolia.*

8. A herbal formulation as claimed in claim 7, wherein X comprises 16–32% by wt of *Centella asiatica,* 4–16% by wt of *Chlorophytum tuberosum,* 5–24% by wt of *Boerhaavia diffusa,* and 12–16% by wt of *Sida cordifolia.*

9. A herbal formulation as claimed in claim 6, comprising 0–16% by wt of *Withania somnifera,* 0–24% by wt of *Pueraria tuberose,* 0–24% by wt of *Asparagus racemosus,* and 0–12% by wt of *Saraca indica.*

10. Herbal formulation as claimed in claim 9, wherein said seeds or seed products are *Glycine max.*

* * * * *